(12) United States Patent
Frazier

(10) Patent No.: US 7,238,151 B2
(45) Date of Patent: Jul. 3, 2007

(54) PERMANENT HEART ASSIST SYSTEM

(76) Inventor: O. Howard Frazier, 3311 Richmond, #350, Houston, TX (US) 77097

( * ) Notice: Subject to any disclaimer, the term of this patent is extended or adjusted under 35 U.S.C. 154(b) by 611 days.

(21) Appl. No.: 10/371,439

(22) Filed: Feb. 21, 2003

(65) Prior Publication Data

US 2003/0163020 A1 Aug. 28, 2003

Related U.S. Application Data

(60) Provisional application No. 60/359,742, filed on Feb. 26, 2002.

(51) Int. Cl.
*A61N 1/362* (2006.01)

(52) U.S. Cl. ..................... 600/16
(58) Field of Classification Search .......... 600/16, 600/17, 18
See application file for complete search history.

(56) References Cited

U.S. PATENT DOCUMENTS

| | | | |
|---|---|---|---|
| 4,105,016 A | 8/1978 | Donovan, Jr. ............ 128/1 D |
| 4,611,578 A * | 9/1986 | Heimes ................ 600/19 |
| 5,267,940 A | 12/1993 | Moulder ................ 600/16 |
| 5,290,277 A | 3/1994 | Plasque | |
| 5,588,812 A | 12/1996 | Taylor et al. ............ 417/356 |
| 5,722,930 A | 3/1998 | Larson, Jr. et al. | |
| 5,924,975 A * | 7/1999 | Goldowsky .............. 600/16 |
| 5,947,892 A * | 9/1999 | Benkowski et al. ....... 600/16 |
| 6,050,975 A * | 4/2000 | Poirier ................. 604/131 |
| 6,066,086 A | 5/2000 | Antaki et al. ............. 600/17 |
| 6,074,180 A | 6/2000 | Khanwilkar et al. ..... 417/356 |
| 6,080,133 A | 6/2000 | Wampler ................ 604/131 |
| 6,093,001 A | 7/2000 | Burgreen et al. ........ 417/423.8 |
| 6,132,363 A | 10/2000 | Freed et al. ............. 600/16 |
| 6,227,820 B1 | 5/2001 | Jarvik ................ 417/423.12 |
| 6,244,835 B1 * | 6/2001 | Antaki et al. ............ 417/356 |
| 6,632,169 B2 | 10/2003 | Korakianitis et al. | |
| 2003/0092961 A1 | 5/2003 | Korakianitis et al. | |

OTHER PUBLICATIONS http://dictionary.reference.com/search?q=percutaneous; See synonyms of percutaneous.*
International Preliminary Examining Authority, "PCT Notification of Transmittal of International Preliminary Examination Report," and cont'd "International Preliminary Examination Report," 4 pgs., PCT/US03/06012, Jan. 23, 2004.
International Preliminary Search Authority, "PCT International Search Report" 5 pgs., PCT/US03/06012, Nov. 25, 2003.

* cited by examiner

*Primary Examiner*—Mark Bockelman
(74) *Attorney, Agent, or Firm*—Jennifer S. Sickler; Gardere Wynne Sewell LLP

(57) ABSTRACT

A heart assist system includes an axial-flow blood pump capable of being implanted in the descending thoracic aorta; a pressure-feedback controller connected to the pump, for controlling the pump, the controller capable of being implanted in the body; and a rechargeable battery pack connected to the pump and to the controller, for providing power to the pump, the battery pack capable of being implanted in the body.

A method for assisting a failing heart comprises the steps of a) in response to when a measured dP/dT signal increases during systole, signaling an implanted aortic blood pump to go into a systolic mode and pump blood at a first flow rate; and b) in response to when the dP/dT signal peaks in the negative region, signaling the pump to go into a diastolic mode and pump blood at a second flow rate.

11 Claims, 6 Drawing Sheets

PERMANENT HEART ASSIST SYSTEM

CROSS-REFERENCE TO RELATED APPLICATIONS

This application claims the benefit of the following U.S. Provisional Application: No. 60/359,742, filed Feb. 26, 2002.

STATEMENT REGARDING FEDERALLY SPONSORED RESEARCH OR DEVELOPMENT

Not Applicable.

REFERENCE TO A "SEQUENTIAL LISTING"

Not Applicable.

BACKGROUND OF THE INVENTION

FIELD OF THE INVENTION

The present invention relates generally to methods and devices for mechanically assisting the failing heart. More specifically, it relates to methods and devices for cardiac support using implantable blood pumps and control system algorithms.

The major causes of death and disability in the industrialized countries of the world remain coronary artery disease, cardiac arrhythmias, and heart failure. Heart failure is the common terminal pathway, of a range of heart diseases. Advances in the therapy of coronary and valvular heart disease have not provided a cure; rather, have provided a life extension with heart failure being the end-event.

Heart failure is a major healthcare problem in the United States. According to the National Heart, Lung and Blood Institute, heart failure is the most rapidly growing cardiovascular disease problem in the United States. It is estimated that 5 million Americans have heart failure, and each year nearly 500,000 people are newly diagnosed with heart failure. Over the past decade, the annual number of hospitalizations has increased from approximately 550,000 to nearly 900,000 for heart failure as a primary diagnosis and from 1.7 to 2.6 million for heart failure as a primary or secondary diagnosis. Nearly 300,000 patients die of heart failure each year and the number of deaths have increased steadily despite advances in treatment.

Heart failure is primarily a disease of the elderly. Approximately 6% to 10% of people older than 65 years have heart failure and approximately 80% of the hospitalized patients with heart failure are more than 65 years old. Heart failure is the most common Medicare-related diagnosis, and more Medicare dollars are spent for the diagnosis and treatment of heart failure than for any other diagnosis. It is estimated that the total costs for treating heart failure in the United States is approximately $40 billion annually. In short, heart failure is a common, costly, disabling, and generally fatal disorder. Alternate surgical and mechanical approaches for treating end-stage heart failure are needed.

Many types of cardiac assist devices have been developed over the past 40 years. The goal of these devices is to mechanically support the failing heart by increasing systemic perfusion, and/or reducing the workload of the failing heart, thus creating the most favorable environment for cardiac recovery.

Results of a major clinical trial for the surgical treatment of end-stage heart failure were presented in November 2001. The Randomized Evaluation of Mechanical Assistance for Treatment of Congestive Heart Failure (REMATCH) trial compared survival and quality of life for patients with advanced heart failure. Patients underwent treatment with an implantable Left Ventricular Assist Device (LVAD) plus drug therapy versus drug therapy alone. The LVAD (HeartMate; Thoratec, Inc.) is a mechanical device that pumps blood in a pulsatile manner from the native left ventricle to the aorta. Originally, LVADs were used as a bridge to cardiac recovery, or as a bridge to cardiac transplantation for patients with advanced heart failure. The REMATCH investigators used the device as long-term therapy for 61 patients who were not candidates for heart transplants and compared outcome with 68 patients who received medical treatment only. Over the course of the 3-year study, LVAD-treated patients lived longer having a mean survival of 408 days compared with 150 days for those on medical therapy alone. Additionally, the LVAD-treated patients demonstrated a significantly better quality of life (exercise capacity, state of mind) when compared with patients who received conventional medical care without the device.

The annual incidence of advanced heart failure in the United States is in the tens of thousands. Homograft (human-to-human) heart transplantation is limited by organ-donor availability, with less than 2,500 heart transplants performed yearly. Xenotransplants (animal-to-man) and the growing of organs for transplant (tissue engineering) are years away, if they will ever provide a solution to this problem. A mechanical assist device, such as the HeartMate LVAD, is immediately available and, in principle, could be used in a large number of patients. However, the major barrier to wide-spread clinical LVAD use may be economic. The estimated cost of the LVAD is $50,000 to $70,000. Therefore, the annual cost for the LVAD alone could range up to $7 billion, worldwide.

DESCRIPTION OF RELATED ART

The following patents disclose magnetically suspended axial flow blood pumps. The full disclosures of these patents are all incorporated herein by this reference:

| | |
|---|---|
| 6,227,820 | Axial force null position magnetic bearing and rotary blood pumps which use them |
| 6,093,001 | Rotary pump having a bearing which dissipates heat |
| 6,080,133 | Sealless rotary blood pump |
| 6,074,180 | Hybrid magnetically suspended and rotated centrifugal pump apparatus and method |

The following patents disclose axial flow blood pumps. The full disclosures of these patents are all incorporated herein by this reference:

| | |
|---|---|
| 6,050,975 | Control of tissue growth in textured blood-contacting surfaces |
| 5,588,812 | Implantable electric axial flow blood pump |
| 5,267,940 | Cardiovascular flow enhancer and method of operation |
| 4,105,016 | Heart pump |

The following patents disclose control systems for implantable blood pumps. The full disclosures of these patents are all incorporated herein by this reference:

| | |
|---|---|
| 6,132,363 | Cardiovascular support control system |
| 6,066,086 | Speed control system for implanted blood pumps |

Because of the limitations with left ventricle to aorta bypass pumps, and the complications associated with "in-parallel" cardiac bypass pumps, there is a need for an improved permanent heart assist system. The existing heart pumps are all placed in the heart ventricle itself. What is needed is a blood pump designed to be placed in the aorta, or sewn into the descending thoracic aorta.

BRIEF SUMMARY OF THE INVENTION

A heart assist system for obtaining a desired end-systolic aortic pressure comprises an axial-flow blood pump for unloading the left ventricle of the heart, the pump capable of being implanted in the descending thoracic aorta; a pressure-feedback controller connected to the pump, for controlling the pump, the controller capable of being implanted in the body; and a rechargeable battery pack connected to the pump and to the controller, for providing power to the pump, the battery pack capable of being implanted in the body.

In another feature of the invention, the heart assist system may be magnetically suspended without the need for bearings. In another feature of the invention, electrical power to the implanted heart assist system may be via percutaneous or transcutaneous energy transmission methods to an implantable rechargeable battery pack. In another feature of the invention, the heart assist system resides inside the descending thoracic aorta, and the drive magnets are placed circumferentially around the outside of the aorta, or may be sewn in with a graft. The impeller can be magnetically suspended without the need for bearings. The heart assist system may be implanted through a thoracotomy approach, but may also be adapted for paracorporeal implantation.

A method for assisting a failing heart comprises the steps of a) implanting an axial-flow blood pump in the descending thoracic aorta of a human; b) sensing the intraventricular pressure of the heart, indicated by dP/dT signals; c) sensing when the dP/dT signal increases during systole; d) in response to when the dP/dT signal increases during systole, signaling the pump to go into a systolic mode and pump blood at a first flow rate; e) sensing when the dP/dT signal peaks in the negative region; and f) in response to when the dP/dT signal peaks in the negative region, signaling the pump to go into a diastolic mode and pump blood at a second flow rate appropriate for the diastolic phase of the cardiac cycle.

The heart assist system provides long-term circulatory support to the failing heart. A pump in the system pump functions as a systolic augmentation device for direct ventricular unloading, that is, a left ventricular assist system. The decreased end-systolic aortic pressure results in ventricular unloading and augmentation of systemic perfusion (stroke volume and cardiac output). In another feature of the method of the present invention, during cardiac diastole, the heart assist system flow rate may be reduced, held constant, or increased, thereby maintaining or increasing diastolic perfusion pressure. The constant flow may augment diastolic pressure, thereby enhancing end organ diastolic perfusion and improving end organ function.

In another feature of the method of the present invention, the heart assist system pumps blood from the patient's upper to the patient's lower arterial compartments.

The present invention is designed to permanently assist the failing human heart for a period of several months to several years. The objectives of the heart assist system of the present invention are to increase cardiac output and systemic perfusion, and to reduce the workload and oxygen requirements of the failing heart, allowing increased levels of patient activity (i.e., exercise) without the signs of circulatory congestion. In addition, the heart assist system requires minimal surgical intervention for insertion and removal with reduced trauma to the failing heart by eliminating the need for direct cannulation of the left atrium or left ventricle. Compared to conventional left ventricular assist systems, the invention avoids direct cannulation of the left ventricle or atrium as required for cardiac bypass devices, yet maintains pulsatile flow and perfusion pressures.

These and other features, objects, and advantages of the invention will be apparent from the description that follows.

BRIEF DESCRIPTION OF THE SEVERAL VIEWS OF THE DRAWINGS

The present invention may be more completely and easily understood when taken in conjunction with the accompanying line drawings, in which.

DETAILED DESCRIPTION OF THE INVENTION

Figure 1:
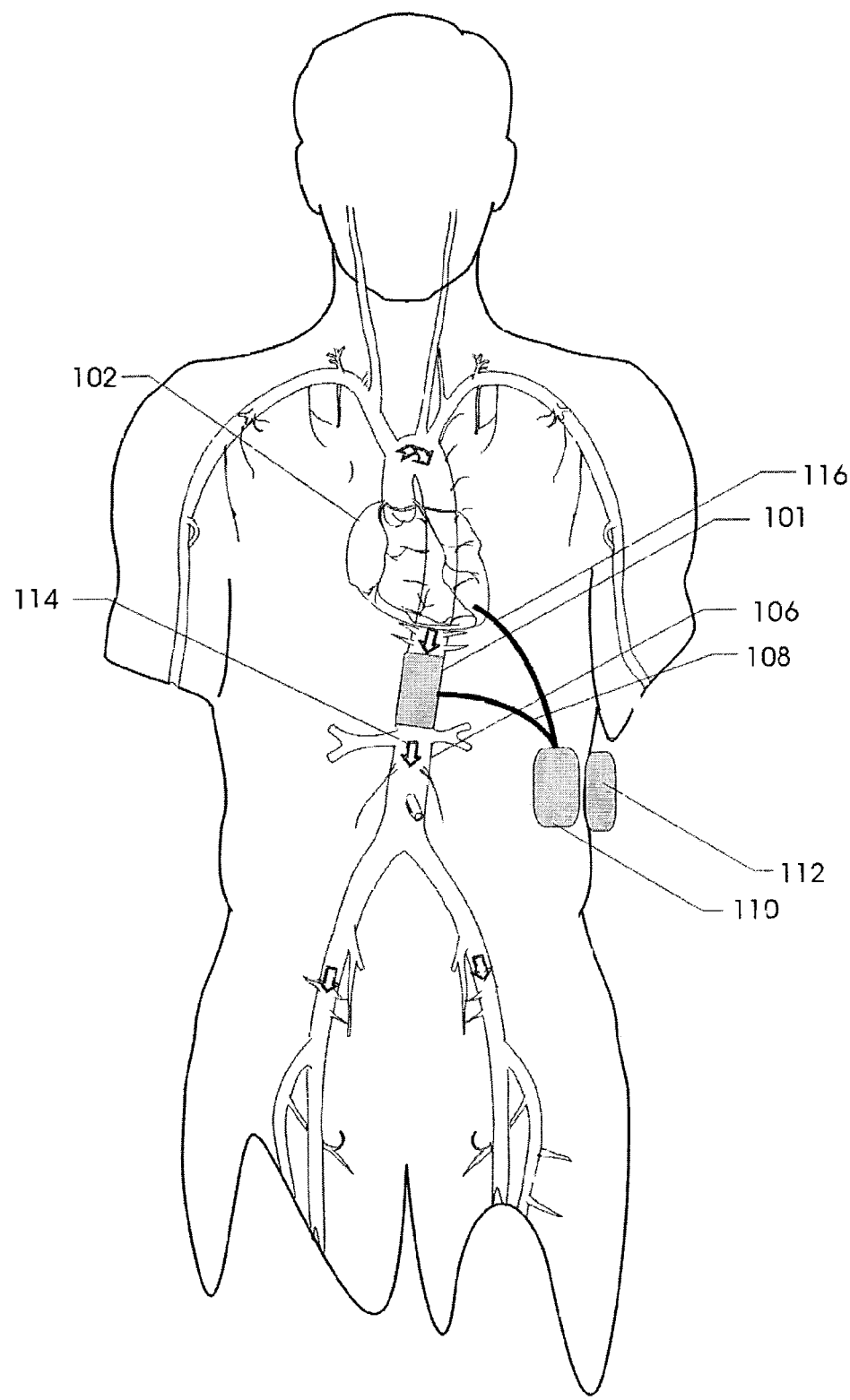
FIG. 1 is a simplified illustration of the heart assist system showing the device placement inside a human.

FIG. 1 illustrates a human with an implanted heart assist system, or axial-flow blood pump, 101 of the present invention. The pump 101 is shown implanted downstream from the natural heart 102, in the descending thoracic aorta 106. The pump 101 is attached directly inside of, and to, the descending thoracic aorta 106, which eliminates the need for a graft. The pump 101 is tethered via a cable 108 to a power and control source 110, which is a microprocessor-based pressure-feedback controller. The power and control source 110 is also implanted in the patient. A rechargeable battery pack 112 is located outside the body, and includes a battery that can be recharged. The battery pack 112 provides power transcutaneously or percutaneously to the power and control source 110, which controls the pump 101 via cable 108. Blood flow is in the direction shown by arrows 114. Pressure sensor 116 measures the pressure in the ventricle of the heart 102. The pressure sensor 116 couples to the power and control source 110.

Figure 2:
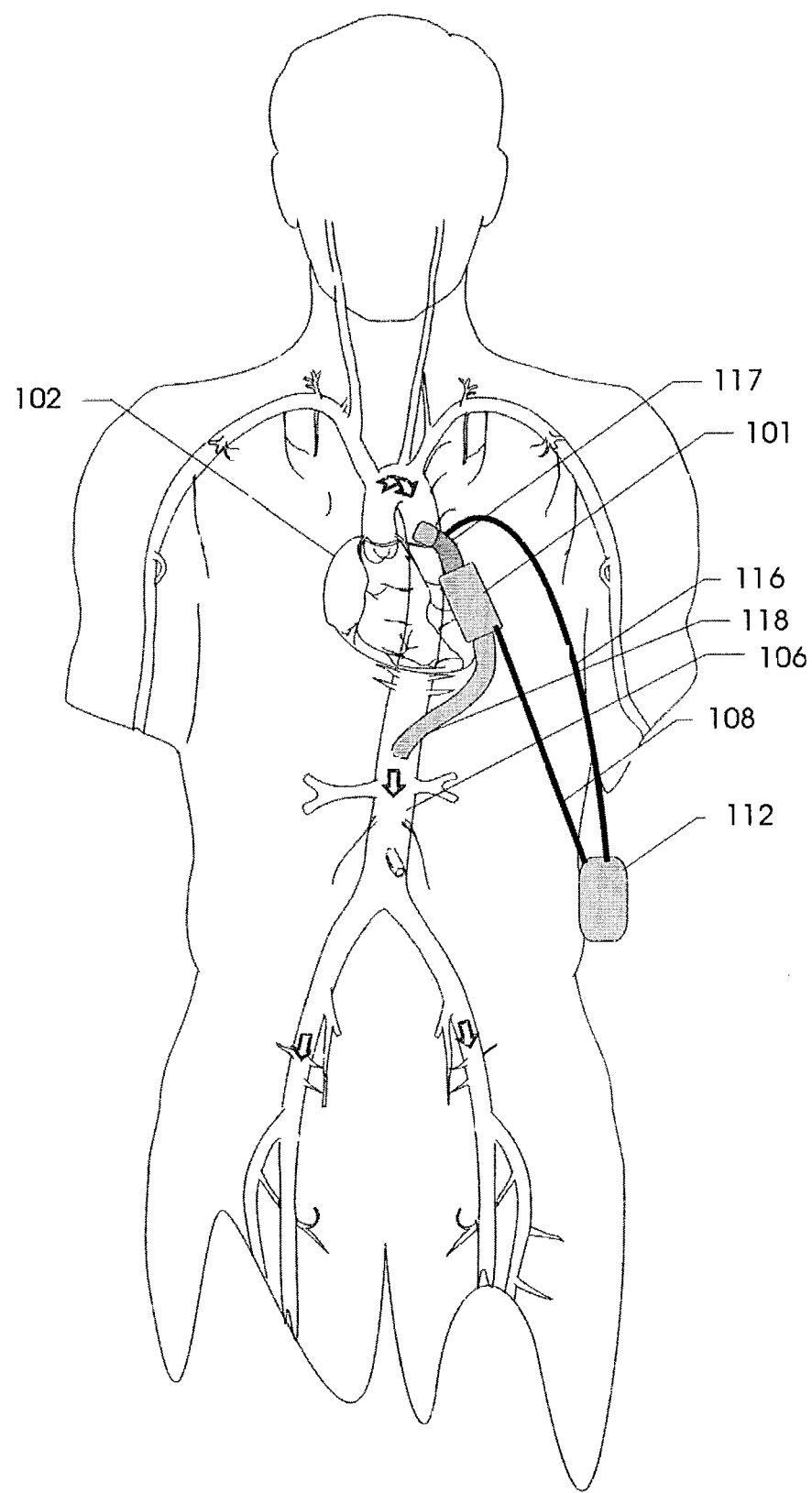
FIG. 2 is a simplified illustration of the heart assist system showing paracorporeal implantation.

FIG. 2 illustrates a human with a paracorporeal implantation of the pump 101. The pump 101 takes blood from the descending thoracic aorta 106 via a graft 117 into the pump 101, and returns blood flow back into the descending thoracic aorta 106 via a graft 118. The pump 101 is outside of the body. One end of the cable 108 is attached to the power and control source 112, while the other end is routed into the inflow conduit of the pump 101 as shown, and then guided into the left ventricle of the heart 102, or can be percutaneously inserted through the skin and into the left ventricle.

Figure 3:
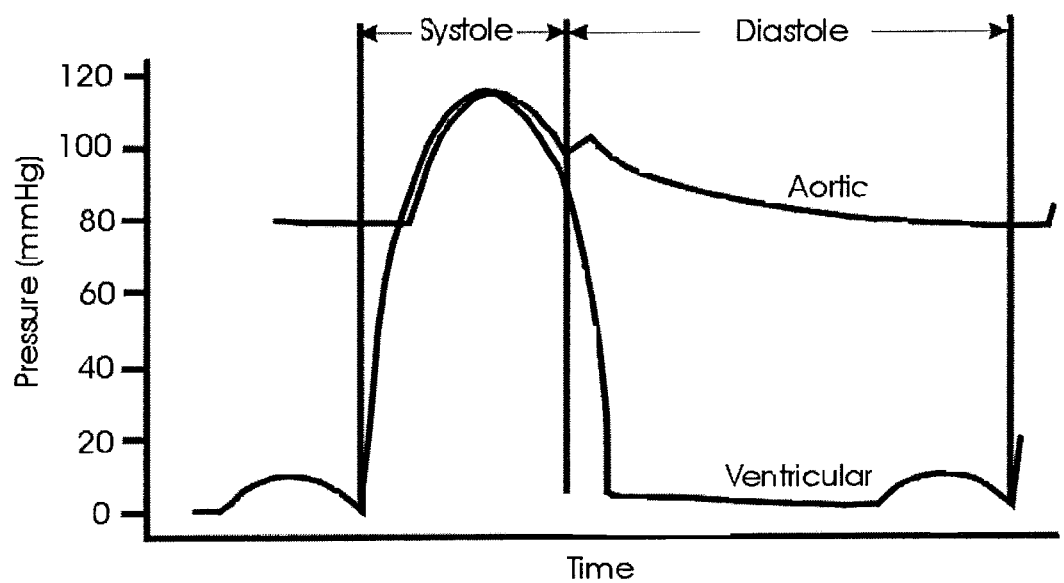
FIG. 3 is an illustration of the aortic and ventricular pressure waveforms of the cardiac cycle.

FIG. 3 illustrates the pressure waveforms during the cardiac cycle. The aortic waveform is shown superimposed on the ventricular waveform. During systole, the ventricle contracts until sufficient pressure is obtained to open the aortic valve. Once the aortic valve opens, blood flow occurs into the systemic system. As the ventricle empties of blood, pressure falls until the aortic valve closes, marking the end of systole. During diastole, the ventricle fills with blood, while the closure of the aortic valve maintains pressure in the systemic bed.

Figure 4:
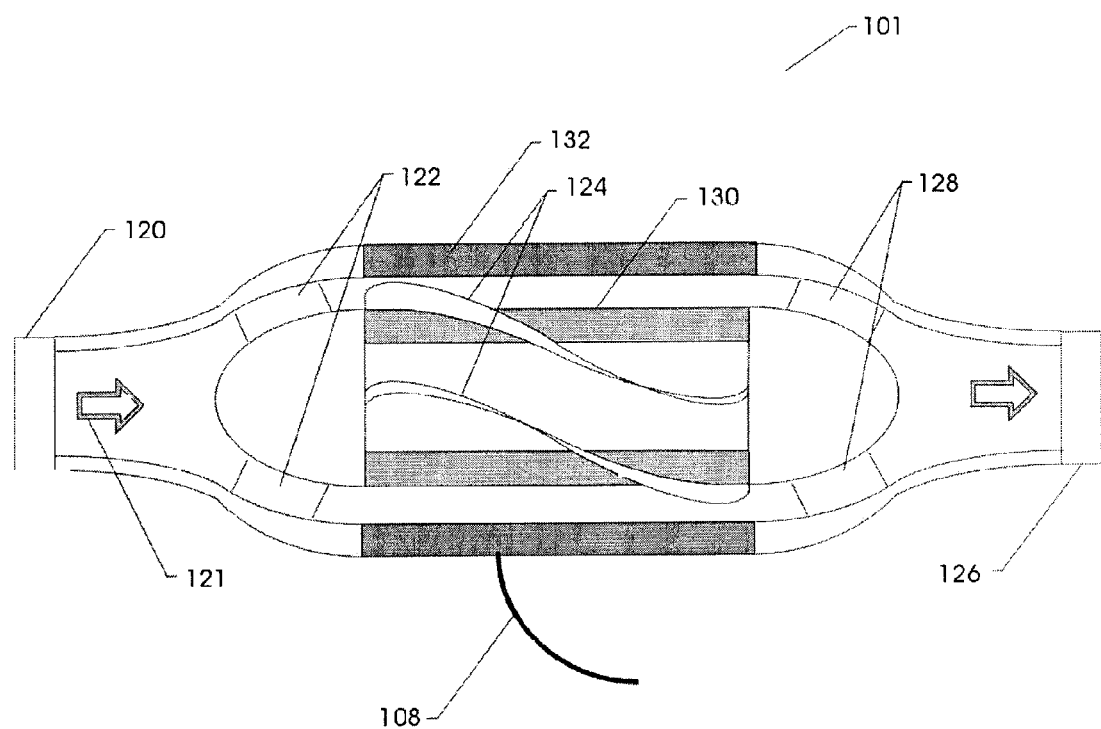
FIG. 4. is an illustration of the heart assist system.

FIG. 4 illustrates in greater detail the pump 101. As blood enters an inflow portion 120 of the pump 101, in the direction shown by an arrow 121, the blood travels past flow straighteners 122 before contacting rotating blades 124, where pressure and flow is increased. Blood exits the pump at location 126, after going past rear flow straighteners 128. The blades 124 rotate in a housing which has magnets 130 at or very near the top of the surface and are arranged circumferentially. Another set of magnets 132 lie circumferentially on the outside of the pump housing and are energized via the cable 108. In the preferred embodiment, the magnets 130 and 132 are magnetically suspended. This eliminates the need for bearings as bearings provide a source of wear to the pump, trauma to the blood, and offer a potential site for thrombosis.

Figure 5A:
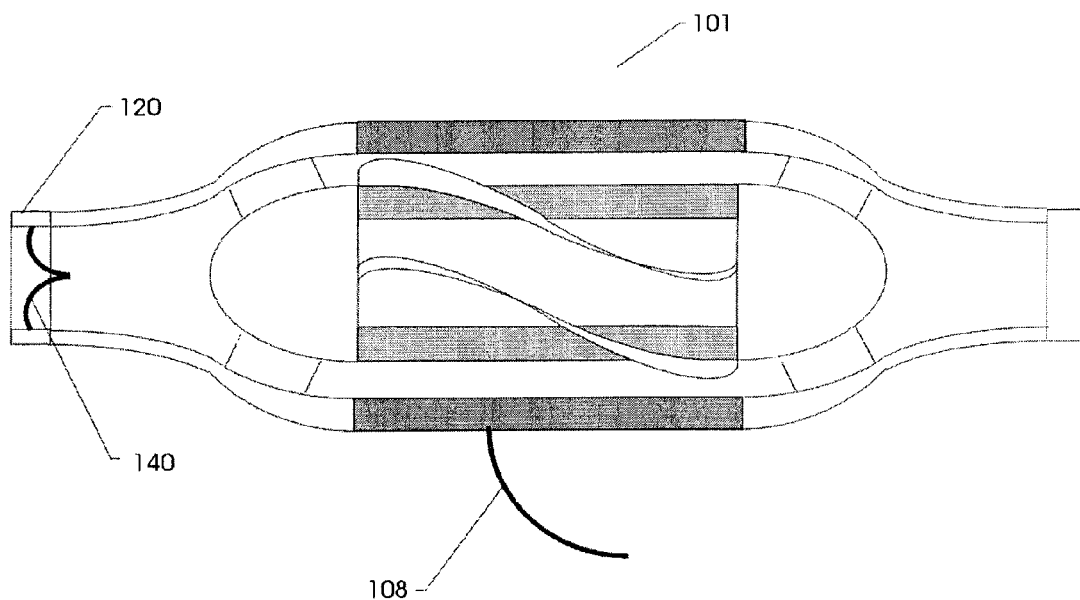
FIG. 5. is an illustration of the heart assist system with an inlet valve.
Figure 5B:
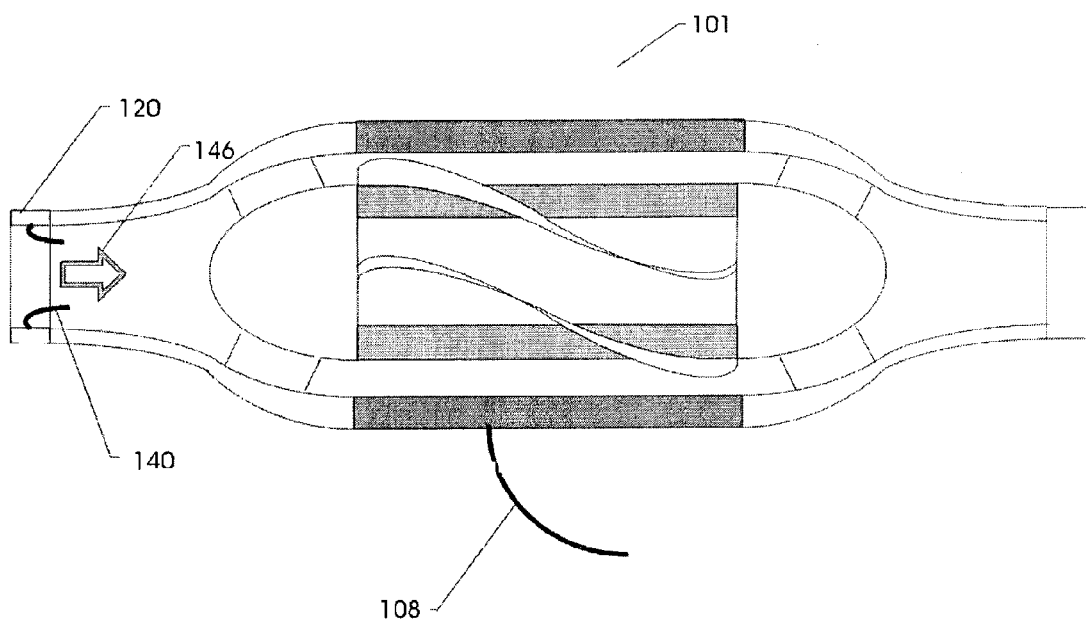

FIG. 5 illustrates another embodiment of the present invention. FIG. 5A illustrates the addition of a valve 140, preferably a tricuspid valve shown to be a part of the inflow portion 120 of the pump 101. FIG. 5A shows the valve 140 in the closed position during diastole. FIG. 5B shows the valve 140 in the open position which would permit flow into the pump 101 as shown by arrow 146 during systole.

Figure 6:
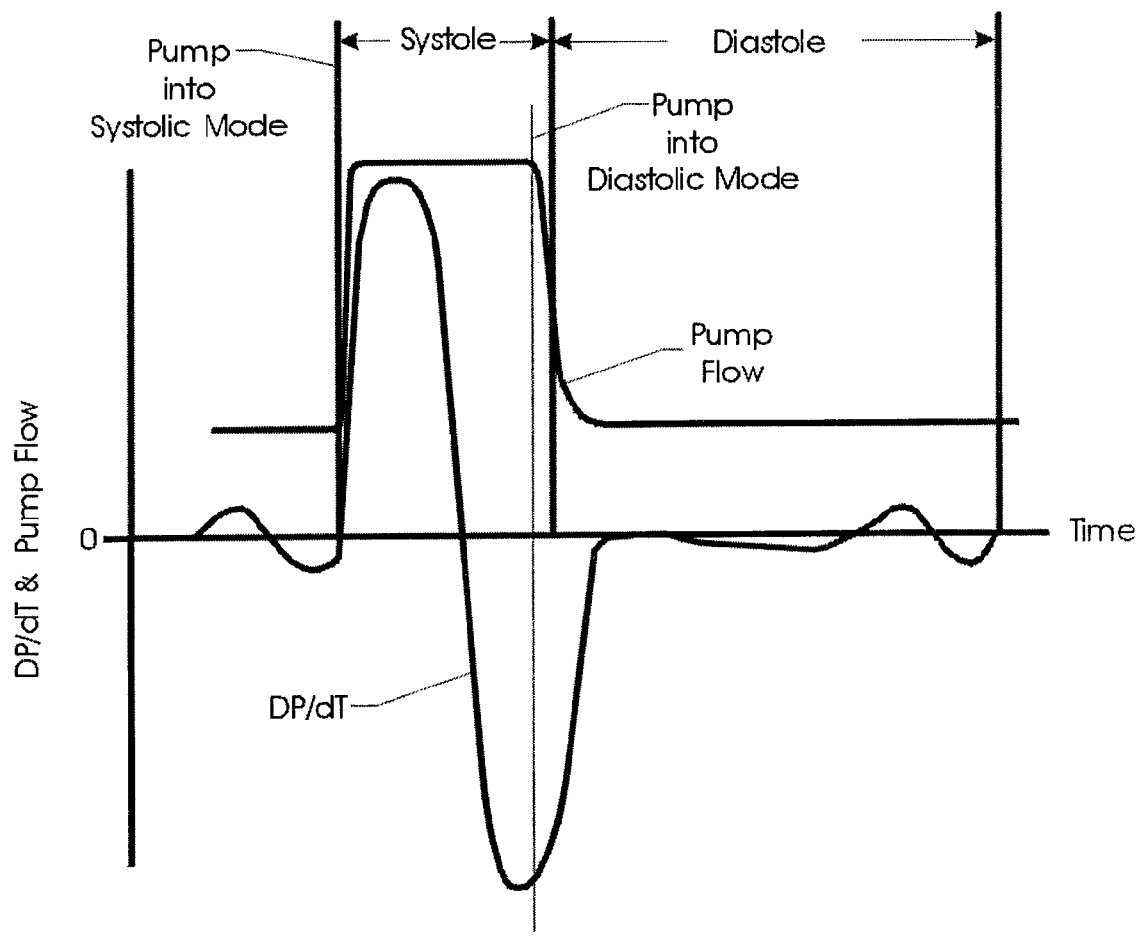
FIG. 6. is a graph showing the first derivative of intraventricular pressure versus time and the flow of the pump over time. Time is represented over one cardiac cycle.

FIG. 6 is a graph of dP/dT with respect to time, where dP/dT represents the first mathematical derivative of ventricular pressure "P" over time "T". The systolic time plus the diastolic time represents the dP/dT of ventricular pressure over one cardiac cycle. Pump flow versus time is also illustrated in FIG. 6. It can be seen in FIG. 6 that during systole the dP/dT has large peaks, and as such would make a good indicator as to when the ventricle is pumping. It is this feature that the power and control source 110 uses to control the pump 101. The pressure sensor 116 measures intraventricular pressure, and outputs pressure signals to the power and control source 110, which evaluate the pressure signals, and operates the pump 101 based on these signals. Using the dP/dT signal, the power and control source 110 recognizes early systole as the early upswing of this parameter, and thus energizes the pump 101 as illustrated in the graph. The pump 101 operates to lower the work effort of the heart, because the pump undertakes a significant portion of the work needed to maintain organ perfusion during this portion of the cardiac cycle. Once the dP/dT signal peaks in early systole, it will fall below the zero line, and become negative before reversing and moving back up toward the zero line. It is in this region, where dP/dT peaks in the negative, that the power and control source 110 signals the pump 101 to go into a diastolic mode. In diastole, the pump 101 operates and pumps blood, but at a lower rate. Pumping blood during diastole will augment diastolic pressure and enhance organ perfusion, improving organ function. Like the "Temporary Heart-Assist System", Ser. No. 10/106,744, the heart assist system flow rate is regulated to obtain a specific end-systolic aortic pressure. The complete disclosure of Ser. No. 10/106,744 is incorporated herein by this reference.

In another embodiment, the power and control source 110 turns the pump 101 off during diastole, there is no blood flow during diastole, and the valve 140 acts to prevent backflow.

In summary, the present invention includes a method for assisting a failing heart, by unloading the left ventricle of the heart, comprising the steps of:

a. implanting an axial-flow blood pump in the descending thoracic aorta of a human;
b. sensing the intraventricular pressure of the heart, indicated by dP/dT signals;
c. sensing when the dP/dT signal increases during systole;
d. in response to when the dP/dT signal increases during systole, signaling the pump to go into a systolic mode and pump blood at a first flow rate;
e. sensing when the dP/dT signal peaks in the negative region; and
f. in response to when the dP/dT signal peaks in the negative region, signaling the pump to go into a diastolic mode and pump blood at a second flow rate appropriate for the diastolic phase of the cardiac cycle.

If desired, the second flow rate may be may be reduced, held constant, or increased, thereby maintaining or increasing diastolic perfusion pressure.

In the above description, a pressure sensitive approach to driving an axial flow device to provide ventricular unloading and enhancing cardiac output has been taught. Further, the pump has a unique method of implantation inside the body, directly to the descending thoracic aorta, without the need for prosthetic grafts.

From the foregoing detailed description, it is apparent that the present invention provides a method and apparatus for mechanically assisting the failing heart. It should be understood that the invention is not intended to be limited to the specifics of the described preferred embodiments, but is defined by the accompanying claims.

What is claimed is:

1. A heart assist system for obtaining a desired end-systolic left ventricular pressure, in a heart containing a mitral valve and an aortic valve, the system comprising:
    a. a continuous, axial-flow blood pump having an impeller, and a drive stator having magnets the pump for volume unloading the left ventricle of the heart, the impeller capable of being implanted completely inside of the descending thoracic aorta and the drive stator configured to be placed around the outside of the aorta,
    b. a ventricular pressure derivative-feedback controller connected to the pump, for controlling the pump impeller's speed, the controller capable of being implanted in the body; and capable of sensing and reacting to closure of the mitral valve, and to closure of the aortic valve, and
    c. a rechargeable battery pack connected to the pump and to the controller, for providing power to the pump, the battery pack capable of being implanted in the body.

2. The system of claim 1, wherein the pump is capable of being sown into the descending thoracic aorta with the use of a graft.

3. The system of claim 2, wherein the pump impeller is magnetically suspended, without the need for bearings.

4. The system of claim 3, wherein the pump is capable of operating in a pressure sensitive mode, with forward flow only during cardiac systole.

5. The system of claim 4, further comprising a distal valve at the pump outlet to eliminate diastolic back flow.

6. The system of claim 5, wherein the pump is capable of electric operation via transcutaneous power transmission.

7. The system of claim 5, wherein the pump is capable of electric operation via percutaneous power transmission.

8. A method for assisting a failing heart, by unloading the left ventricle of the heart, comprises the steps of:
   a. implanting an axial-flow blood pump impeller completely inside of the descending thoracic aorta of a human implanting a drive stator having magnets outside of the descending aorta,
   b. sensing the intraventricular pressure of the heart, indicated by dP/dT signals;
   c. sensing when the dP/dT signal increases during systole;
   d. in response to when the dP/dT signal increases during systole, signaling the pump to go into a systolic mode and pump blood at a first flow rate;
   e. sensing when the dP/dT signal peaks in the negative region; and
   f. in response to when the dP/dT signal peaks in the negative region, signaling the pump to go into a diastolic mode and pump blood at a second flow rate appropriate for the diastolic phase of the cardiac cycle.

9. The method of claim 8, wherein the second flow rate is reduced from the first flow rate.

10. The method of claim 8, wherein the second flow rate is held substantially the same as the first flow rate.

11. The method of claim 8, wherein the second flow rate is increased from the first flow rate.

* * * * *